(12) United States Patent
Smith et al.

(10) Patent No.: US 11,344,305 B2
(45) Date of Patent: *May 31, 2022

(54) CLOSURE DEVICE WITH FIXED JAW HOOK

(71) Applicant: BOSTON SCIENTIFIC SCIMED, INC., Maple Grove, MN (US)

(72) Inventors: Paul Smith, Smithfield, RI (US); Matthew R. Jagelski, Marlborough, MA (US); Naroun Suon, Lawrence, MA (US); Kevin J. McElwee, Franklin, MA (US); Shawn Ryan, Littleton, MA (US); Alex Sekulic, Salisbury, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 300 days.

This patent is subject to a terminal disclaimer.

(21) Appl. No.: 16/706,237

(22) Filed: Dec. 6, 2019

(65) Prior Publication Data
US 2020/0107831 A1 Apr. 9, 2020

Related U.S. Application Data

(63) Continuation of application No. 15/589,620, filed on May 8, 2017, now Pat. No. 10,537,328.
(Continued)

(51) Int. Cl.
*A61B 17/10* (2006.01)
*A61B 17/122* (2006.01)
(Continued)

(52) U.S. Cl.
CPC ........ *A61B 17/10* (2013.01); *A61B 17/00234* (2013.01); *A61B 17/083* (2013.01);
(Continued)

(58) Field of Classification Search
CPC ............ A61B 17/00234; A61B 17/083; A61B 17/1227; A61B 17/1285;
(Continued)

(56) References Cited

U.S. PATENT DOCUMENTS 3,882,854 A * 5/1975 Hulka ................ A61B 17/1285
600/104
8,734,469 B2 * 5/2014 Pribanic ............. A61B 17/0487
606/142
(Continued)

FOREIGN PATENT DOCUMENTS

CN 102065781 5/2011
CN 102791200 11/2012
(Continued)

*Primary Examiner* — Jocelin C Tanner
(74) *Attorney, Agent, or Firm* — Fay Kaplun & Marcin, LLP

(57) ABSTRACT

A device includes a capsule extending longitudinally from a proximal end to a distal end and including a channel extending therethrough. The capsule is releasably coupled to a proximal portion of the device. Device also includes a first arm rigidly fixed to the distal end of the capsule to extend distally therefrom. In addition, Device includes a second arm, a proximal end of which is slidably received within the capsule so that the second arm is movable between an open configuration, in which the second arm is moved laterally away from the first arm and a distal end of the second arm is moved distally past the distal end of the first arm, and a closed configuration, in which the second arm is moved toward the first arm and the distal end of the second arm is moved proximally toward the distal end of the first arm.

12 Claims, 7 Drawing Sheets

Related U.S. Application Data

(60) Provisional application No. 62/333,615, filed on May 9, 2016.

(51) Int. Cl.
*A61B 17/00* (2006.01)
*A61B 17/08* (2006.01)
*A61B 17/128* (2006.01)

(52) U.S. Cl.
CPC ...... *A61B 17/1227* (2013.01); *A61B 17/1285* (2013.01); *A61B 2017/0034* (2013.01); *A61B 2017/00526* (2013.01); *A61B 2017/00584* (2013.01); *A61B 2017/00818* (2013.01); *A61B 2017/00867* (2013.01)

(58) Field of Classification Search
CPC .. A61B 2017/0034; A61B 2017/00526; A61B 2017/00584; A61B 2017/00818; A61B 2017/00867
See application file for complete search history.

(56) References Cited

U.S. PATENT DOCUMENTS

| | | | |
|---|---|---|---|
| 10,537,328 B2 * | 1/2020 | Smith | A61B 17/00234 |
| 2007/0135678 A1 * | 6/2007 | Suzuki | A61B 17/1227 600/37 |
| 2014/0171974 A1 * | 6/2014 | Zhu | A61B 17/122 606/144 |
| 2014/0243586 A1 * | 8/2014 | Rohaninejad | A61B 17/2833 600/37 |

FOREIGN PATENT DOCUMENTS

| | | |
|---|---|---|
| CN | 107072671 | 8/2017 |
| CN | 101588760 | 11/2019 |
| EP | 3305215 | 4/2018 |

* cited by examiner

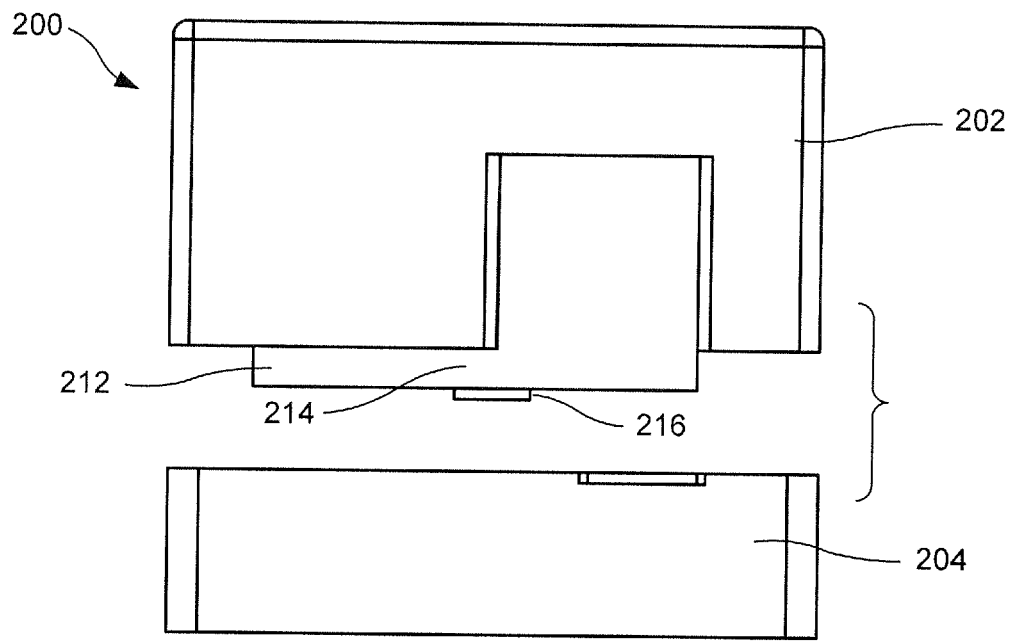
F I G. 14
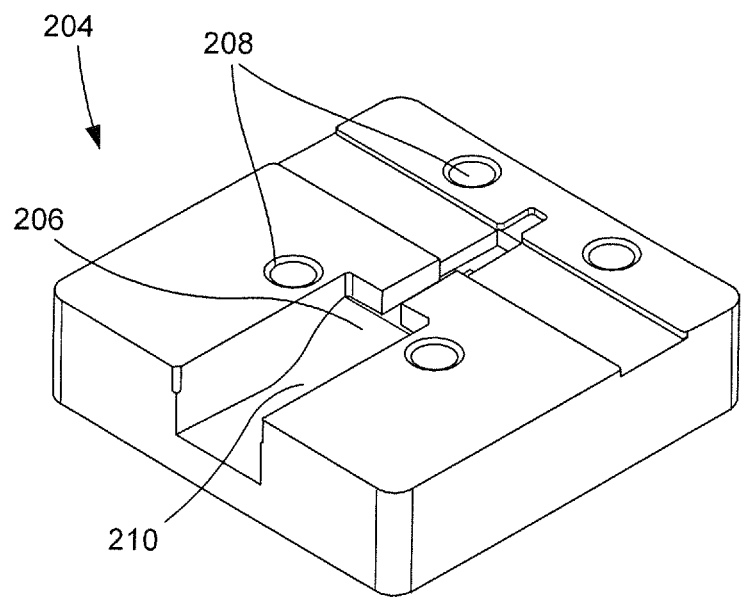
F I G. 15

# CLOSURE DEVICE WITH FIXED JAW HOOK

The present application is a Continuation of pending U.S. patent application Ser. No. 15/589,620 filed May 8, 2017, which claims priority to U.S. Provisional Patent Application Ser. No. 62/333,615 filed May 9, 2016; the disclosure of which is incorporated herewith by reference.

BACKGROUND

Physicians have become more willing to perform more aggressive interventional and therapeutic endoscopic procedures including, for example, removal of larger lesions (e.g., cancerous masses), tunneling under mucosal layers in the gastro-intestinal (GI) tract to treat tissues below the mucosa, full thickness removal of tissue, inserting devices through the GI tract and then penetrating the GI organ to treat tissue outside the GI tract, and endoscopic treatment/repair of post-surgical issues (e.g., post-surgical leaks, breakdown of surgical staple lines, anastomotic leaks). These procedures may increase the risk of perforating or damaging the wall of the GI tract, or may require closure of the GI tract wall as part of the procedure. Endoscopic closure can reduce the cost, trauma and inconvenience associated with these procedures. However, conventional endoscopic tissue closure devices may be insufficient to close certain tissue defects.

SUMMARY

The present invention is directed to a device for treating a tissue comprising a capsule extending longitudinally from a proximal end to a distal end and including a channel extending therethrough, the capsule releasably coupled to a proximal portion of the device and a first arm rigidly fixed to the distal end of the capsule to extend distally therefrom in combination with a second arm, a proximal end of which is slidably received within the capsule so that the second arm is movable between an open configuration, in which the second arm is moved laterally away from the first arm and a distal end of the second arm is moved distally past the distal end of the first arm, and a closed configuration, in which the second arm is moved toward the first arm and the distal end of the second arm is moved proximally toward the distal end of the first arm.

In an embodiment, the first arm extends along an axis substantially parallel to a longitudinal axis of the capsule.

In an embodiment, the distal end of the first arm includes a tissue piercing member extending laterally inward toward the second arm.

In an embodiment, the second arm is biased toward the open configuration and is restrained via an interior surface of the capsule in the closed configuration.

In an embodiment, the second arm is formed of a compliant material.

In an embodiment, the compliant material includes one of Nitinol and Stainless Steel.

In an embodiment, an interior surface of one of the first and second arms include a hook, undercut and barb for catching a target tissue.

In an embodiment, an interior surface of the first arm is curved so that longitudinal edges thereof extend toward the second arm to form a cupped tissue receiving pocket.

In an embodiment, the first arm includes a broad interior surface forming a tissue receiving pocket in one plane.

In an embodiment, the interior surface includes one of teeth, spikes, grooves and a textured surface to grip tissue received between the first and second anus.

The present disclosure also relates to a method for forming a superelastic Nitinol arm for a tissue clipping device comprising: inserting Nitinol stock in a recess of a female portion of a die assembly, the recess sized and shaped to have a desired geometry of the arm for the tissue clipping device; mating a male portion of the die assembly to the female portion, the male portion including a geometrically complementary protrusion sized and shaped to be received within the recess of the female portion to configure the Nitinol stock to have the desired geometry of the arm; placing the mated male and female portions of the die assembly in a fluidic bath having a temperature of approximately 500° to treat the Nitinol stock having the desired geometry; and removing the die assembly from the fluidic bath and water quenching the die assembly to set the Nitinol stock in the desired geometry.

In an embodiment, the die assembly is removed from the fluidic bath and water quenched once the Nitinol stock reaches 500° C.

In an embodiment, water quenching cools the Nitinol stock to room temperature.

In an embodiment, the recess of the female portion includes a curved portion to form a corresponding curve in the arm.

In an embodiment, the protrusion of the male portion includes a portion for stamping out a desired feature in the arm.

The present disclosure also relates to a method for treating a tissue defect, comprising: inserting a clipping device, in a closed configuration, to a target area within a living body via a working channel of an endoscope, the clipping device including a capsule, a first arm rigidly fixed to a distal end of the capsule and extending distally therefrom and a second arm movably received within the capsule; moving the clipping device from the closed configuration to an open configuration, in which the second arm is moved laterally away from the first arm and a distal end of the second arm is moved distally past a distal end of the first arm; piercing a first tissue along a first side of a tissue defect with the distal end of the first arm; moving the clipping device toward a second tissue along a second side of the tissue defect, the second side opposing the first side; grasping the second tissue with the distal end of the second arm; and moving the clipping device toward the closed configuration, in which the second arm is drawn laterally toward the first arm and the distal end of the second arm is drawn proximally toward the distal end of the first arm so that the second tissue is drawn toward the first tissue, thereby closing the tissue defect.

In an embodiment, the clipping device is moved toward the closed configuration prior to moving the clipping device toward the second tissue and is moved toward the open configuration prior to grasping the second tissue.

In an embodiment, the method includes locking the clipping device in the closed configuration and deploying the clipping device.

In an embodiment, the clipping device is moved between the open and closed configurations via a control element releasably coupled to the proximal end of the second arm, the control element being released from the second arm to deploy the clipping device.

In an embodiment, in the closed configuration, the distal ends of the first and second arms are substantially longitudinally aligned.

BRIEF DESCRIPTION

FIG. 14 shows a side view of the die assembly of FIG. 13; and

FIG. 15 shows a perspective view of a female die of the die assembly of FIG. 13.

DETAILED DESCRIPTION

Figure 1:
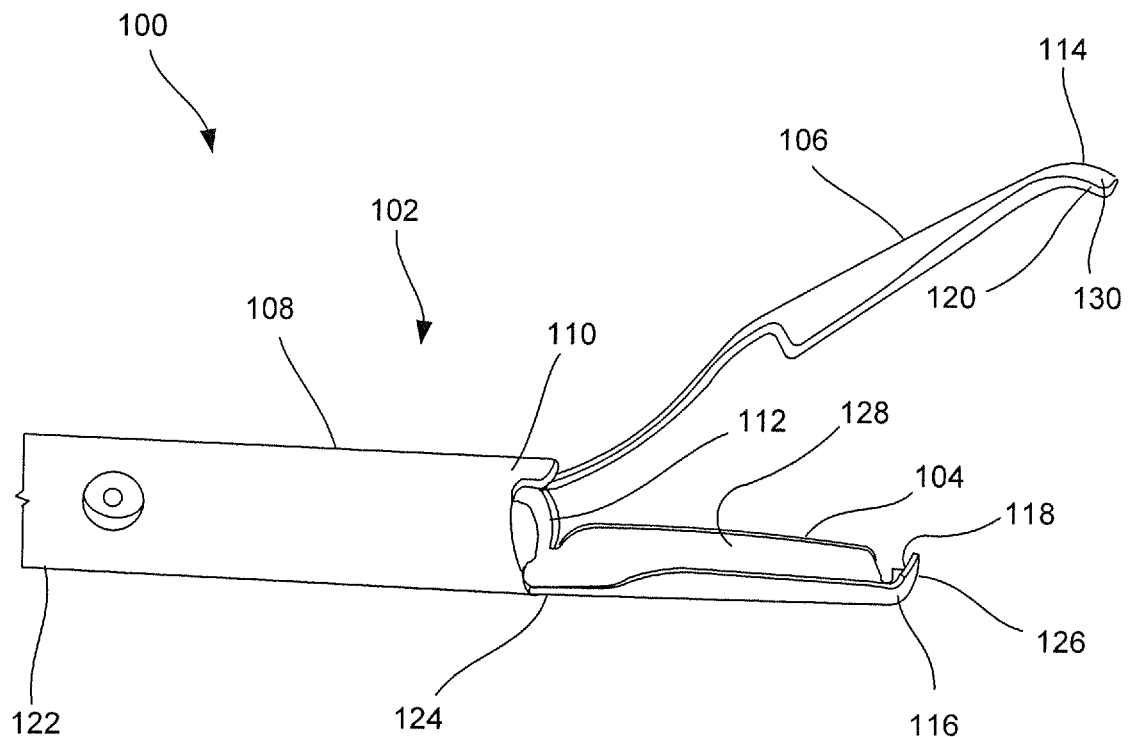
FIG. 1 shows a longitudinal side view of a device according to a first exemplary embodiment of the present disclosure, in an open configuration.

The present disclosure may be further understood with reference to the following description and the appended drawings, wherein like elements are referred to with the same reference numerals. The present disclosure is directed to an endoscopic clipping device for treating tissue perforations, defects and/or bleeding. In particular, exemplary embodiments of the present disclosure describe an endoscopic clip including a first jaw rigidly fixed to a capsule and a second jaw slidably housed within the capsule to be moved between an open configuration and a closed configuration. In the open configuration, a distal end of the second jaw extends laterally away from and distally past a distal end of the first jaw so that target tissue may be received therebetween. In the closed configuration, the second jaw is retracted into the capsule so that the second jaw is moved laterally inward and the distal end of the second jaw is moved toward the distal end of the first jaw to grip the target tissue therebetween. It should be noted that the terms "proximal" and "distal," as used herein, are intended to refer to a direction toward (proximal) and away from (distal) a user of the device.

Figure 2:
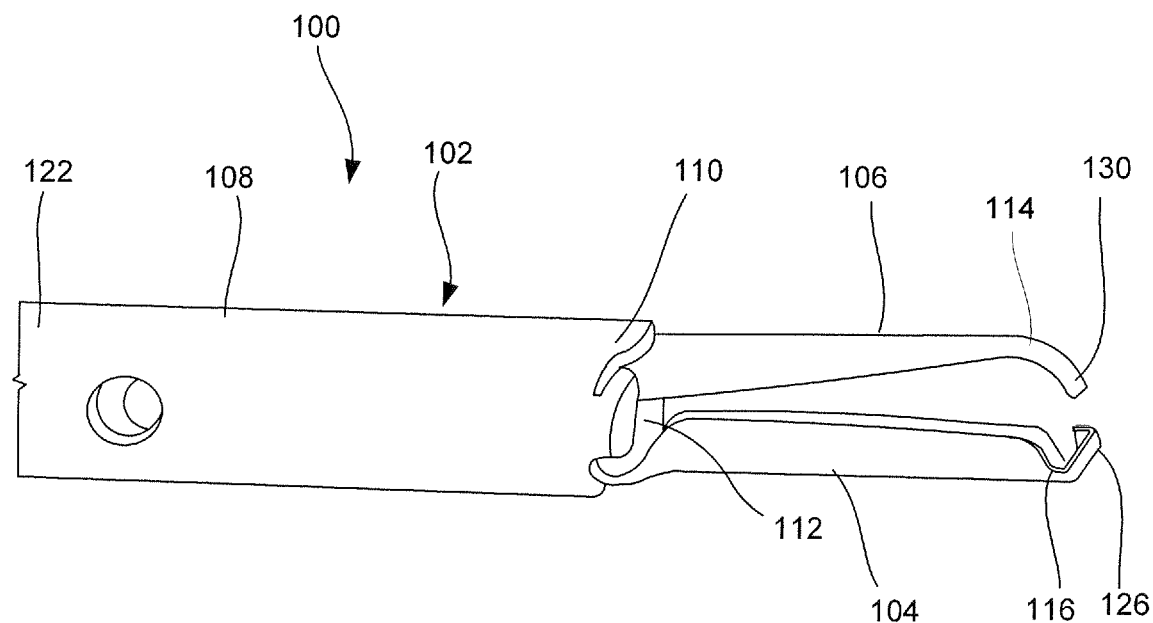
FIG. 2 shows a longitudinal side view of the device of FIG. 1, in a closed configuration.

As shown in FIGS. 1-9, a clipping device 100 according to an exemplary embodiment of the present disclosure comprises a clip 102 insertable into a living body through, for example, a working channel of an endoscope to a target tissue to be treated. The clip 102 is releasably connected to a proximal portion that is sufficiently flexible to permit it to be passed through the endoscope even when the endoscope is traversing tortuous paths of the body—e.g., passing through the working channel of an endoscope inserted through a natural body lumen accessed via a natural body orifice. For example, the proximal portion may include a flexible member formed of a coil of wire or any other suitable, flexible structure. As shown in FIGS. 1-2, the clip 102 includes a first arm 104 rigidly fixed to a distal end 110 of a capsule 108 and a second arm 106 slidably received within a longitudinal channel 112 of the capsule 108. The clip 102 is movable between an open configuration, in which a distal end 114 of the second arm 106 extends laterally away from and distally of a distal end 116 of the first arm 104, and a closed configuration, in which the distal end 114 of the second arm 106 extends toward the first arm 104 so that the distal end 114 of the second arm 106 is substantially longitudinally aligned with the distal end 116 of the first arm 104. In use, as shown in FIGS. 6-9, the clip 102 is inserted to a target area of the living body and moved to the open configuration so that a first capture feature 118 of the first arm 104 captures a first portion of tissue along a first side of a tissue defect to be treated. With the first portion of tissue captured by the first arm 104, the clip 102 is moved toward a second side of the tissue defect so that a second capture feature 120 on the second arm 106 may capture a second portion of tissue along the second side of the tissue defect. The clip 102 may then be moved toward the closed configuration so that the first and second portions of tissue are moved toward one another to close the tissue defect. Since the clip 102 allows for approximation of the first and second sides of the tissue defect, the device 100 may be particularly suited to treat large tissue openings/defects.

The capsule 108 extends longitudinally from a proximal end 122 to the distal end 110 and includes the channel 112 extending longitudinally therethrough. The proximal end 122 of the channel 112 is releasably coupled to a flexible member (not shown) of the proximal portion of the device 100 so that the clip 102, including the capsule 108, may be deployed therefrom to be implanted in the body. The capsule 108 may, for example, be coupled to the flexible member via a bushing releasably coupled to the capsule 108 via cantilever arms of the bushing that are received within corresponding windows at the proximal end of the capsule 108, substantially as described in U.S. Patent Appln. Pub. No. 2014/0088616 to Clerc et al. and assigned to Boston Scientific Scimed Inc. ("the '616 application"). The entire disclosure of the '616 application is incorporated herein by reference. The cantilever arms of the bushing may, for example, be biased to disengage from the capsule 108 but are held in position locked into the windows of the capsule by a support structure which is disengaged from the bushing arms when a control element connected to a proximal end of the second arm 106 is separated therefrom. The control element may be coupled to the second arm 106 via a control member, as described in U.S. Patent Appln. Pub. No. 2014/0088616 or, in another embodiment, may be directly coupled to the second arm 106. The control element may be separated from the second arm 106 when the control element is drawn proximally relative to the capsule 108 to exceed a predetermined load. When the control element is separated from the second arm 106, in this embodiment a locking tab of the second arm 106 moves radially outward to engage a portion of the capsule 108, thereby locking the clip 102 in the closed configuration. Although the above describes a specific mechanism for locking and deploying the clip 102, the clip 102 may be deployed from the proximal portion of the device 100 and/or locked in the closed configuration via any of a variety of known clip deployment and locking mechanisms.

Figure 3:
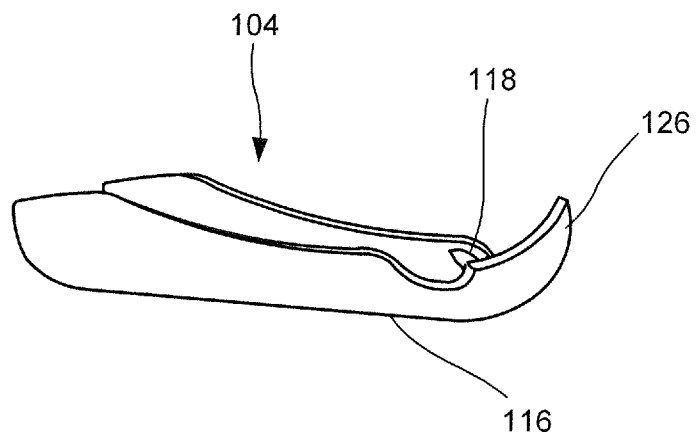
FIG. 3 shows a longitudinal side view of a portion of an arm of the device of FIG. 1.
Figure 4:
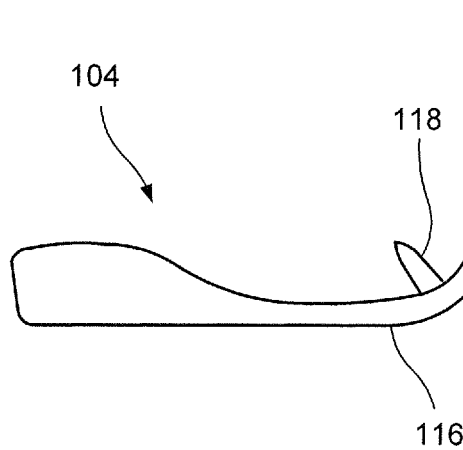
FIG. 4 shows another longitudinal side view of a portion of an arm of the device of FIG. 1.
Figure 5:
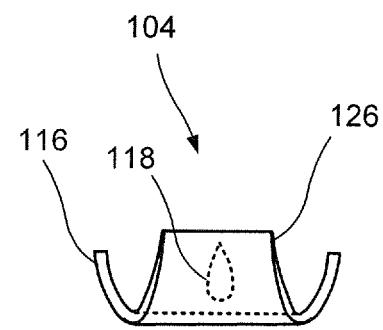
FIG. 5 shows a front view of the portion of the arm of the device of FIG. 4, from a distal end thereof.

The first arm 104 extends distally from the distal end 110 of the capsule 108 to the distal end 116. The first arm 104 in this embodiment is integrally formed with the capsule 108. However, in an alternative configuration, the first arm 104 may be rigidly fixed to the capsule 108 via any known connection mechanism such as, for example, welding. In one embodiment, the first arm 104 extends from the distal end 110 of the capsule 108 along an axis substantially parallel to a longitudinal axis of the capsule 108. The first arm 104 extends from a proximal end 124 connected to the capsule 108 to the distal end 116. The distal end 116 may be curved or bent to include a distal tip 126 that extends laterally inward toward the longitudinal axis of the clip 102 so that the distal tip 126 may hook or grip target tissue received between the first and second arms 104, 106. As shown in FIG. 3, the distal end 116 may also include the first capture feature 118 which may be configured as, for example, an undercut along a side of the first arm 104 facing the second arm 106. Alternatively, or in addition to the undercut, as shown in FIGS. 4-5, the first capture feature 118 may include a barb punched into the first arm 104 to extend toward the second arm 106. The first capture feature 118 may be configured as any of a variety of elements extending from a side or interior surface 128 of the first arm 104 to face toward the second arm 106.

Figure 10:
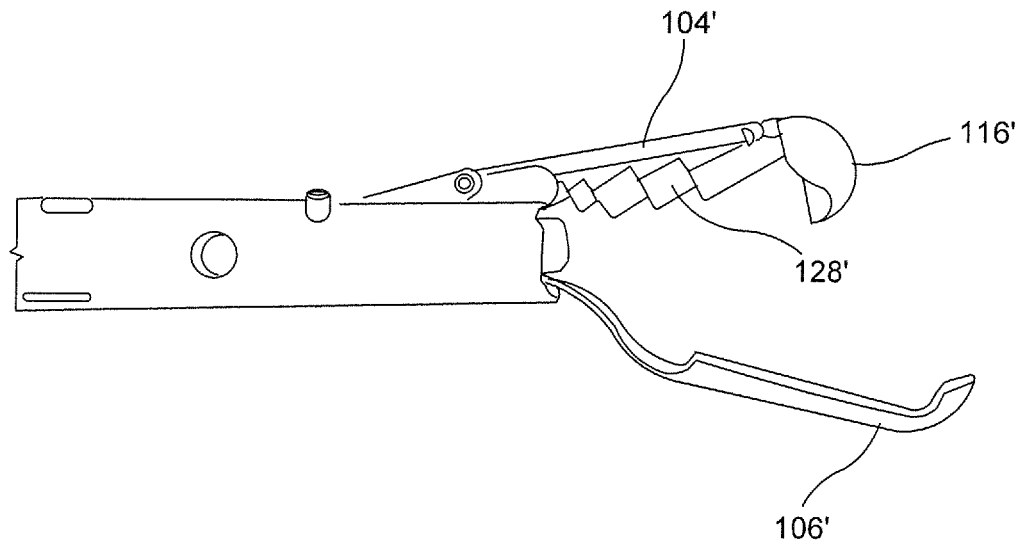
FIG. 10 shows a perspective view of a device according to an alternate embodiment of the present disclosure.

In one embodiment, as shown in FIGS. 1-2, the interior surface of the first arm 104 may be cupped or curved so that longitudinal edges thereof are curved toward the second arm 106 forming a cupped pocket in which tissue may be received. In another embodiment, as shown in FIG. 10, a first arm 104' may have a broad (non-cupped) interior surface 128' which forms a tissue receiving pocket in one plane. The interior surface 128' may include teeth, spikes, grooves and/or a textured surface to provide additional gripping for tissue received between the first and second arms. A distal end 116' of the first arm 104' may also include a hook or other tissue piercing member such as a sharp point or barb for hooking or gripping tissue.

A proximal end of the second arm 106 is slidably received within the channel 112 of the capsule 108 so that the second arm 106 is movable relative thereto between the open and closed configurations. The proximal end of the second arm 106 may be connected to a control element extending proximally therefrom through the capsule 108 and the proximal portion of the device 100 to be controlled by a user. The control element may be moved longitudinally relative to the device 100 to move the clip 102 between the open and closed configurations. The second arm 106 is formed of a compliant material which permits the second arm 106 to be moved between the open and closed configurations. The second arm 106 may be movable between the open and closed configuration via, for example, a living hinge. In one embodiment, the second arm 106 may be biased toward the open configuration so that, when the second arm 106 is moved distally relative to the capsule 108, toward the open configuration, the second arm 106 reverts to the biased configuration and moves laterally away from the first arm 104 as the distal end 114 of the second arm 106 is moved distally past the distal end 116 of the first arm 104. In the closed configuration, the second arm 106 is drawn proximally into the channel 112 and restrained via an interior surface of the capsule 108 so that the second arm 106 is moved laterally toward the first arm 104 as the distal end 114 of the second arm 106 is moved toward the distal end 116 of the first arm 104. In one embodiment, the distal ends 116, 114 of the first and second arms 104, 106, respectively, may be substantially longitudinally aligned in the closed configuration.

Similarly to the first arm 104, the distal end 114 of the second arm 106 may be bent or curved inward to form a distal tip 130 which extends laterally inward toward the longitudinal axis of the clip 102 so that the distal tip 130 hooks and/or grips tissue received between the first and second arms 104, 106. The distal tip 130 may include the second capture feature 120 for gripping tissue such as, for example, a sharp point or barb. Alternatively or, in addition to the tissue gripping features at the distal tip 130, the distal end 114 of the second arm 106 may include tissue gripping/capturing features such as an undercut and/or a barb, as described above in regard to the first arm 104, and as shown in FIGS. 3-5.

Figure 11:
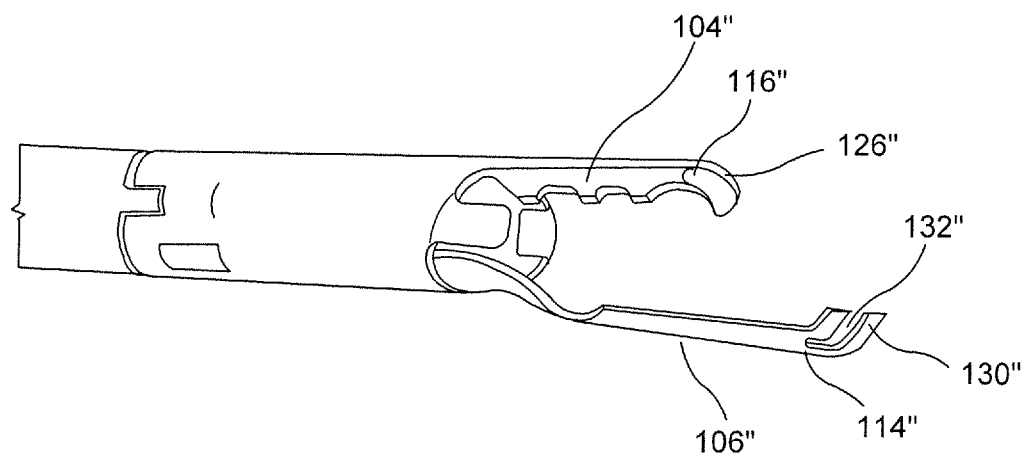
FIG. 11 shows a perspective view of a device according to another alternate embodiment of the present disclosure.

In one embodiment, the distal ends 116, 114 of the first and second arms 104, 106, respectively, are substantially longitudinally aligned in the closed configuration so that the distal tips 126, 130 are substantially aligned and face one another. In another embodiment, as shown in FIG. 11, a distal tip 130" of a second arm 106" includes a window 132" extending therethrough for accommodating a distal tip 126" of a first arm 104" therein. Thus, in the closed configuration, the distal tip 126" of the first arm 104" is received within the window 132" of the second arm 106", when gripping tissue. Alternatively, the second arm 106" may be permitted to be drawn proximally of the first arm 104" so that a distal end 114" of the second arm 106" may be drawn proximally past a distal end 116" of the first arm 104".

Figure 6:
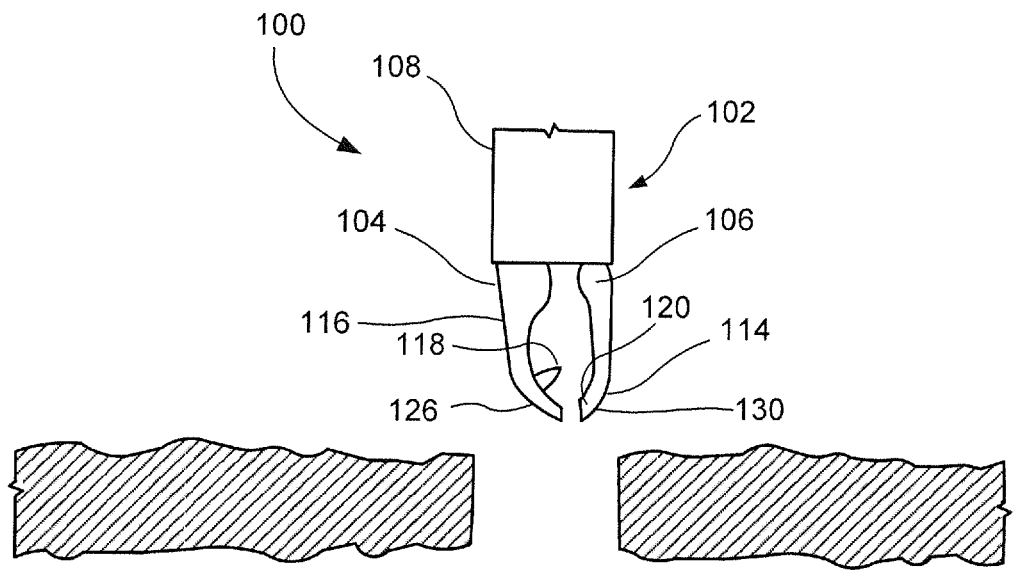
FIG. 6 shows a side view of the device of FIG. 1, inserted to a target tissue in the closed configuration.
Figure 7:
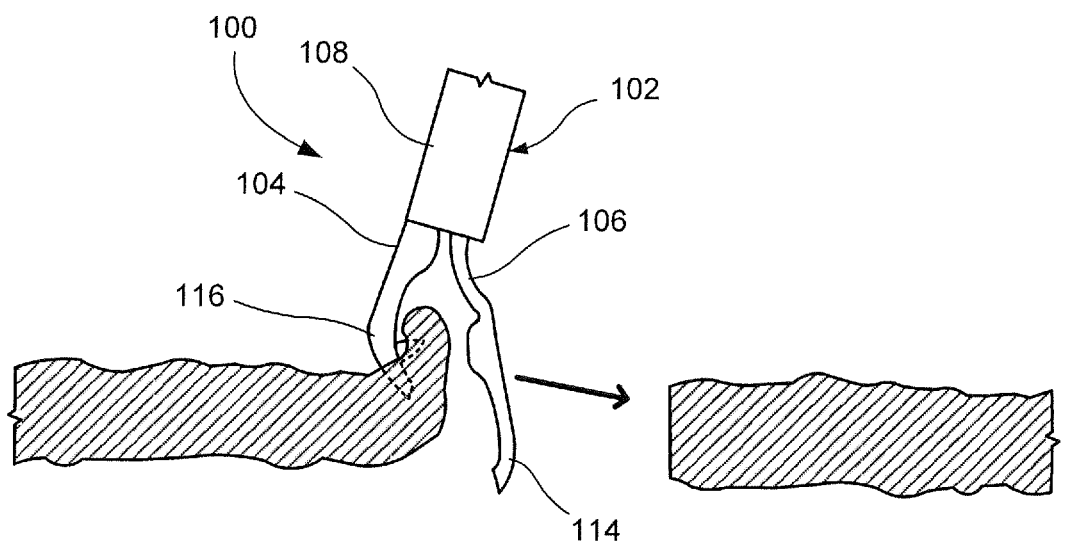
FIG. 7 shows a side view of the device of FIG. 1, a first arm of the device gripping a first side of a tissue defect in the open configuration.
Figure 8:
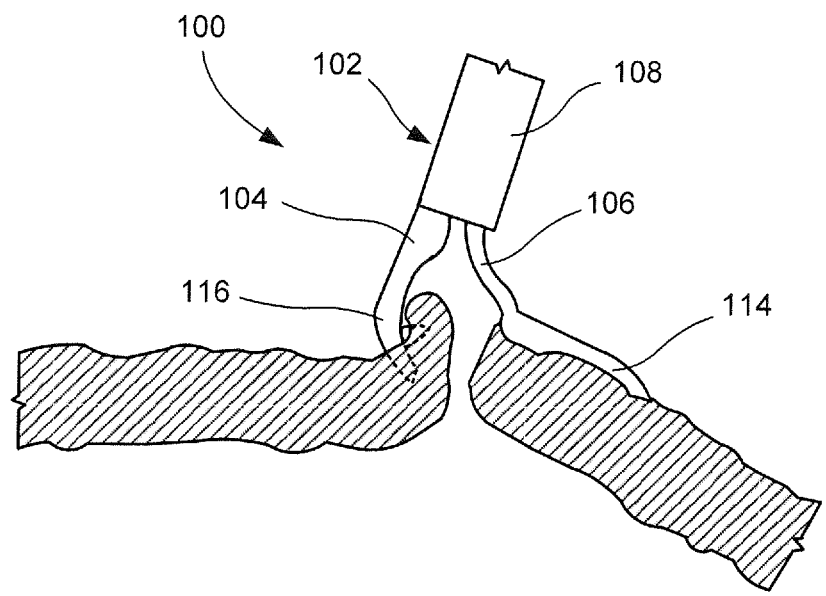
FIG. 8 shows a side view of the device of FIG. 1, a second arm of the device gripping a second side of a tissue defect in the open configuration.

As shown in FIGS. 6-9, an exemplary method utilizing the device 100 comprises inserting the clip 102, in the closed configuration, to a target area within a living body via, for example, a working channel of an endoscope. As described above, the clip 102 is able to approximate separated portions of tissue so that the clip 102 is particularly suited for treating large tissue defects. Once at the target area, as shown in FIG. 6, the clip 102 is moved to the open configuration and manipulated so that the distal end 116 of the first arm 104 hooks or grips a first portion of tissue along a first side of the tissue defect, as shown in FIG. 7. The first portion of tissue may be captured by the hook at the distal tip 126 of the first arm 104 and/or the first capture feature 118 which may include, for example, an undercut or barb. Once the first portion of tissue has been captured by the first arm 104, the clip 102 is moved toward a second portion of tissue along a second side of the tissue defect—e.g., opposite the first side. Prior to moving the clip 102 toward the second portion of tissue, the clip 102 may be moved toward the closed configuration. Thus, upon reaching the second portion of tissue, the clip 102 is returned to the open configuration so that the second arm 106 is moved laterally and distally relative to the first arm 104 to hook and/or grip the second portion of tissue via the distal end 114 of the second arm 106, as shown in FIG. 8. The second portion of tissue may be captured by the distal tip 130 and/or the second capture feature 120. The gripping features, as described with respect to FIGS. 10 and 11, may be used to provide greater grippage of the first and second portions of tissue between the first and second arms 104, 106.

Figure 9:
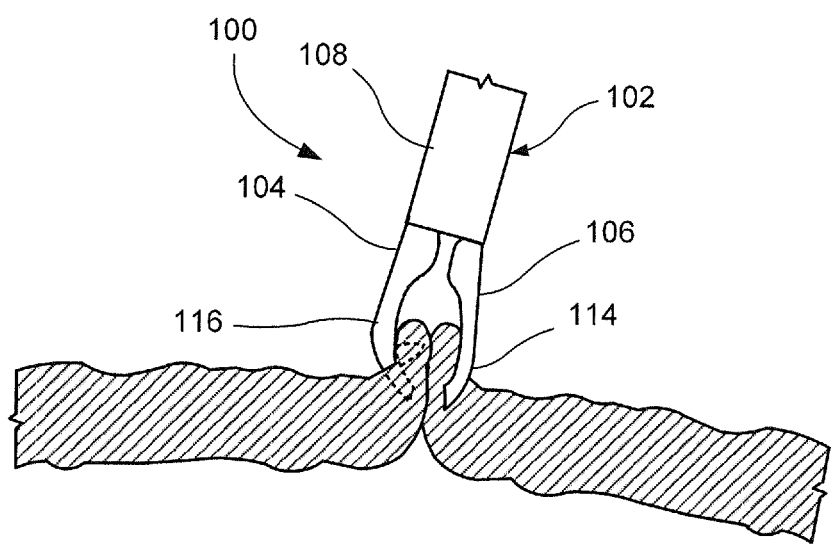
FIG. 9 shows a side view of the device of FIG. 1, moved to the closed configuration to close the tissue defect.

Once the second portion of tissue has been captured/hooked, the clip 102 is moved to the closed configuration to draw the second arm 106 toward the first arm 104. As described above, the second arm 106 is moved laterally toward the first arm 104 as the distal end 114 of the second arm 106 is moved toward the distal end 116 of the first arm 104, as shown in FIG. 9, thereby drawing the first and second portions of tissue captured via the distal ends 116, 114, respectively, toward one another. Thus, tissue along the first and second sides of the tissue defect are drawn together to close the tissue defect. Once the tissue defect has been closed, as desired, the clip 102 may be locked in the closed configuration and deployed to separate it from the proximal portion of the device 100, as would be understood by those skilled in the art. For example, the control element connected to the proximal end of the second arm 106 may be drawn proximally relative to the capsule 108 until a predetermined threshold load is exceeded and the control element is separated from the second arm 106. Separation of the control element from the second arm 106 in this embodiment then allows a locking tab of the second arm 106 to engage the capsule 108, thereby locking the second arm 106 relative thereto, in the closed configuration. Proximal motion of the control element also facilitates release of the capsule 108 from the proximal portion of the device 100, thereby releasing the clip 102 so that it will remain in the body when the proximal portion of the device 100 is withdrawn from the body. The clip 102 will then be sloughed off as the natural healing process progresses as would be understood by those skilled in the art.

Figure 12:
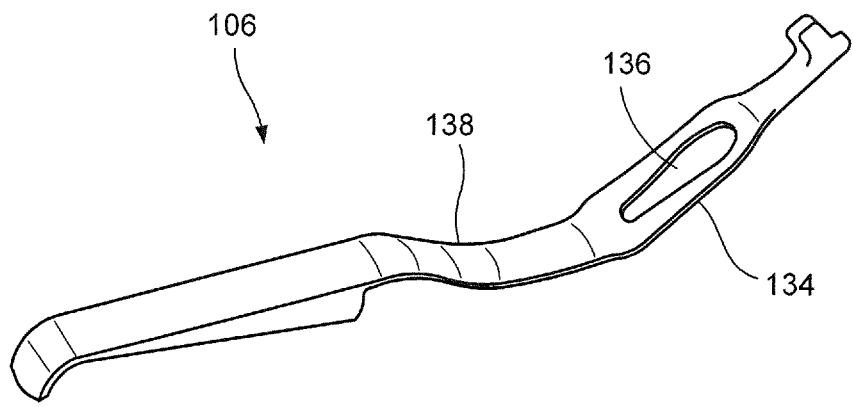
FIG. 12 shows a perspective view of an arm of the device of FIG. 1.
Figure 13:
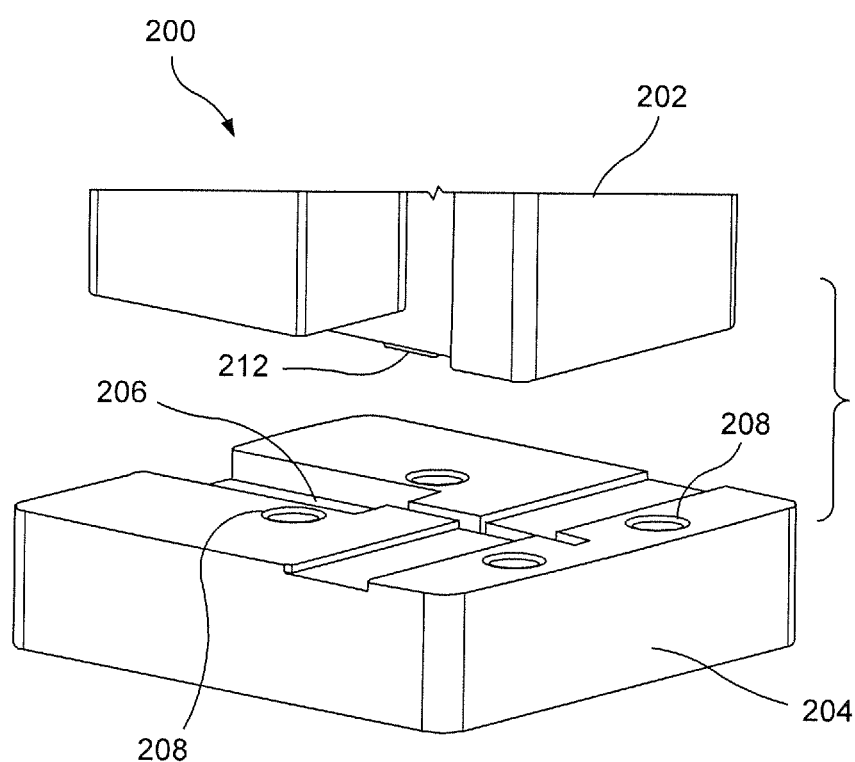
FIG. 13 shows a perspective view of a die assembly according to an exemplary embodiment of the present disclosure.

As described above, the second arm 106 of the clip 102 may, for example, be formed of a compliant material such as, for example, Nitinol. In one embodiment, the second arm 106, as shown in FIG. 12, may be formed via a superelastic Nitinol forming process, which includes a die assembly 200, as shown in FIGS. 13-15, comprising a male die 202 and a female die 204 that are created to configure the Nitinol in the desired geometry. The die assembly 200 potentially increases the precision of the feature set in the Nitinol material and allows multiple sheets of metal to be formed at once, thereby decreasing cost and increasing volume output capabilities. Unlike conventional Nitinol forming processes, the male and female dies 202, 204 are not required to be attached to any machinery such as, for example, a press. Rather, the male and female dies 202, 204 may include mating features such as, for example, bolts or pins, which allow the dies 202, 204 to be joined together while housing the Nitinol stock so that the Nitinol stock is configured to the desired geometry. The joined male and female dies 202, 204 with the configured Nitinol would then be placed in a fluidic bath set at approximately 500° C. to treat the Nitinol. For example, the Nitinol may be treated at a temperature of between 450 and 550 degrees C. for from 2 to 20 minutes. In one embodiment, after treating the Nitinol for approximately 10 minutes at 55 degrees C., the die assembly 200 is removed from the bath and immediately water quenched so that the Nitinol material retains its desired shape. Water quenching ensures that the Nitinol components are cooled immediately to room temperature, thereby limiting the amount of time in which the Nitinol components remain at high temperature. Ideally, the Nitinol components are cooled immediately after the Nitinol has reached 500° C. Thus, although the above method describes treating the Nitinol for approximately 10 minutes, this time may vary depending on the amount of time it takes to heat the Nitinol to 500° C.

To create the desired Nitinol component (e.g., the second arm 106 shown in FIG. 12), the die assembly 200 is created in 3D form so that complex geometry features may be created in the Nitinol. For example, as shown in FIGS. 13 and 15, the female die 204 of the die assembly 200 includes a recess 206 sized and shaped to create the desired size and shape of the second arm 106. The recess 206 may include a curved portion 208 along a portion of a length thereof to create a corresponding radii 138 in the second arm 106, which biases the arm 106 toward the open configuration, as described above. The female die 204 may also include openings 210 for receiving mating features such as, for example, bolts or pins, for joining the male die 202 to the female die 204.

The male die 202, as shown in FIGS. 13 and 14, may include a geometrically complementary protrusion 212 sized and shaped to be received within the recess 206 of the female die 204 so that when the male and female dies 202, 204 are mated or joined to one another, the Nitinol stock received within the recess 206 is molded to the desired size and shape of the second arm 106. For example, the protrusion may include a first portion 214 sized and shaped to stamp out a shape 134 (e.g., rectangular) of a length of the second arm 106 and a second portion 216 protruding from the first portion 214 for adding a feature 136 (e.g., opening) in the second arm 106.

Although the female and male dies 204, 202 are shown and described as including a single recess 206 and complementary protrusion 212, respectively, the die assembly 200 may be designed to include multiple recesses 206 and protrusions 212 so that multiple arms 106 may be formed at a time, reducing cost while increasing volume output. In addition, although the male and female dies 202, 204 are described as including particular design features, the male and female dies 202, 204 may include any of a variety of geometrical features designed to create a desired geometry of the second arm 106.

Variations may be made in the structure and methodology of the present disclosure, without departing from the spirit and the scope of the disclosure. Thus, it is intended that the present disclosure cover the modifications and variations of this disclosure that may be contemplated by a person of skill in the art.

What is claimed is:

1. A device for treating a tissue, comprising:
a capsule extending longitudinally from a proximal end to a distal end and including a channel extending therethrough, the capsule releasably coupled to a proximal portion of a flexible member;
a first arm extending distally between a first arm proximal end rigidly coupled to the distal end of the capsule and a first arm distal end; and
a second arm extending from a second arm proximal end to a second arm distal end, the second arm proximal end being slidably received within the capsule.

2. The device of claim 1, wherein a length of the second arm is greater than a length of the first arm.

3. The device of claim 1, wherein the second arm is movable between an open configuration, in which the second arm angles laterally away from the first arm and the second arm distal end is moved distally past the first arm distal end, and a closed configuration, in which contact between the capsule and the second arm draws the second arm toward the first arm and draws the second arm distal end proximally toward the first arm distal end.

4. The device of claim 3, wherein the second arm is biased toward the open configuration.

5. The device of claim 1, wherein the first arm extends along an axis substantially parallel to a longitudinal axis of the capsule.

6. The device of claim 1, wherein the first arm distal end includes a tissue piercing member extending laterally inward toward the second arm.

7. The device of claim 1, wherein the second arm is formed of a compliant material.

8. The device of claim 7, wherein the compliant material includes one of Nitinol and Stainless Steel.

9. The device of claim 1, wherein an interior surface of one of the first and second arms include a hook, undercut and barb for catching a target tissue.

10. The device of claim 1, wherein an interior surface of the first arm is curved so that longitudinal edges thereof extend toward the second arm to form a cupped tissue receiving pocket.

11. The device of claim 1, wherein the first arm includes a broad interior surface forming a tissue receiving pocket in one plane.

12. The device of claim 11, wherein the interior surface includes one of teeth, spikes, grooves and a textured surface to grip tissue received between the first and second arms.

* * * * *